(12) United States Patent
Sayed et al.

(10) Patent No.: US 10,120,835 B2
(45) Date of Patent: Nov. 6, 2018

(54) LOAD RATING OF BRIDGES, INCLUDING SUBSTRUCTURE

(71) Applicants: Sayed Mourad Sayed, Maitland, FL (US); Hisham Nassim Sunna, Wesley Chapel, FL (US); Pamela Ruth Moore, Longwood, FL (US)

(72) Inventors: Sayed Mourad Sayed, Maitland, FL (US); Hisham Nassim Sunna, Wesley Chapel, FL (US); Pamela Ruth Moore, Longwood, FL (US)

(73) Assignee: GCI, Inc., Longwood, FL (US)

( * ) Notice: Subject to any disclaimer, the term of this patent is extended or adjusted under 35 U.S.C. 154(b) by 564 days.

(21) Appl. No.: 14/665,299

(22) Filed: Mar. 23, 2015

(65) Prior Publication Data

US 2015/0286751 A1 Oct. 8, 2015

Related U.S. Application Data

(60) Provisional application No. 61/976,709, filed on Apr. 8, 2014.

(51) Int. Cl.
*G06F 17/10* (2006.01)
*G01N 3/00* (2006.01)
*G01M 5/00* (2006.01)

(52) U.S. Cl.
CPC ............ *G06F 17/10* (2013.01); *G01M 5/0008* (2013.01); *G01N 3/00* (2013.01)

(58) Field of Classification Search
CPC ......... G06F 17/10; G01M 5/0008; G01N 3/00
USPC ............................................................ 703/1
See application file for complete search history.

(56) References Cited

U.S. PATENT DOCUMENTS 5,355,715 A * 10/1994 Rausche ................. G01L 25/00
 73/1.15
2013/0325367 A1* 12/2013 McVay ................... E21B 44/00
 702/41

OTHER PUBLICATIONS

Caiza et al. (Load Rating and Retrofit Testing of Bridge Timber Piles Subjected to Eccentric Loading, 2012 (66 pages).*

(Continued)

*Primary Examiner* — Andre Pierre Louis
(74) *Attorney, Agent, or Firm* — Volpe and Koenig, P.C.

(57) ABSTRACT

For bridges over waterways which are susceptible to scour, the load carrying capacity of the substructure may be reduced by scour. These bridges must be evaluated for reduced load rating and/or posting limits. Here, the substructure load rating is used in connection with calculating the bridge load rating. This is often limited by the substructure load carrying capacity and the tolerable deformation. Thus, bridges impacted by scour need to be judged based on both the superstructure and substructure components. The system/process to assess the substructure load rating uses an analytical method which combines numerical methods and empirical calculations to predict the behavior of a bridge's superstructure and substructure. Limited instrumentation is installed at critical locations on the bridge. The measurements are then used to verify and refine predictions to arrive at a substructure load rating which is usable with the superstructure load rating to define a safe load carrying capacity.

14 Claims, 7 Drawing Sheets

(56) References Cited

OTHER PUBLICATIONS

Fisher et al. (An Evaluation of Scour Measurement Devices, 2012 (13 pages)).*
Matsui et al. (Difference in estimating layer modulus from static and dynamic back-calculations, 2002 (17 pages)).*
Sayed M. Saved, P.E., M.Asce, et al., "Load Rating of Pile-Supported Bridges Susceptible to Scour", Journal of Bridge Engineering © ASCE/May 2013, pp. 439-449.

* cited by examiner

LOAD RATING OF BRIDGES, INCLUDING SUBSTRUCTURE

INCORPORATION BY REFERENCE

The following documents are incorporated herein by reference as if fully set forth: U.S. Provisional Patent Application No. 61/976,709, filed Apr. 8, 2014.

FIELD OF INVENTION

The present disclosure relates generally to a load rating process and, more specifically, to a load rating process for a bridge supported by a deep foundation consisting of either piles or drilled shafts, whether on land or over waterways.

BACKGROUND

All roadway bridges whether new or existing must be load rated to determine safe live load carrying capacity. A load rating analysis may be performed as part of the design process for new structures. Load rating for existing structures is reviewed regularly and updated based on the observed condition of the superstructure. Detailed calculation procedures, as published by AASHTO and/or the various state highway departments, are followed. In critical cases which warrant the expense, field verification testing may be performed. These procedures do not address substructure load rating other than to point out that the engineer may want to consider it if there is evidence of deterioration. The methodology to be used in this situation is undefined and left to a bridge engineer's judgment. As a result, the substructure load rating is often based on a qualitative rather that a quantitative approach and may not account for soil behavior and soil-structure interaction. There is currently no procedure specific to substructure load rating. Most bridge load ratings are based on analysis of the superstructure only.

SUMMARY OF INVENTION

The load rating process according to the invention analyzes both the superstructure and the substructure of a bridge using modeling and calculations alone or in combination with operational measurements obtained from limited field instrumentation. The process can be used to compute the load rating of a new bridge or an existing bridge.

DETAILED DESCRIPTION OF THE PREFERRED EMBODIMENTS

Figure 1A:
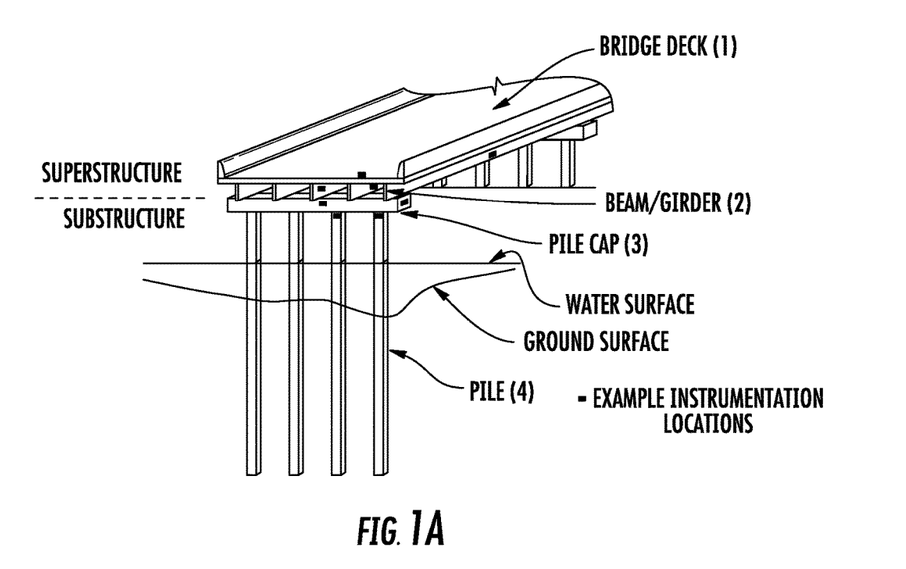
FIG. 1a illustrates a typical bridge pile bent construction

FIG. 1a illustrates a typical bridge pile bent construction. The bent is supported on piles with known or unknown embedment depth. Drilled shafts may be substituted for piles. As illustrated in FIG. 1a, the superstructure generally includes the bridge deck 1 and beams/girders 2. Some structures might have a deck designed as a flat slab cast directly on the substructure. The typical substructure includes the pile (shaft) cap 3 and the piles (shafts) 4. During service, the loads are transferred from the bridge deck to the soil via the beams/girders, pile (shaft) cap, and then the piles (shafts). Therefore, the soil is ultimately carrying the bridge loads.

Figure 1B:
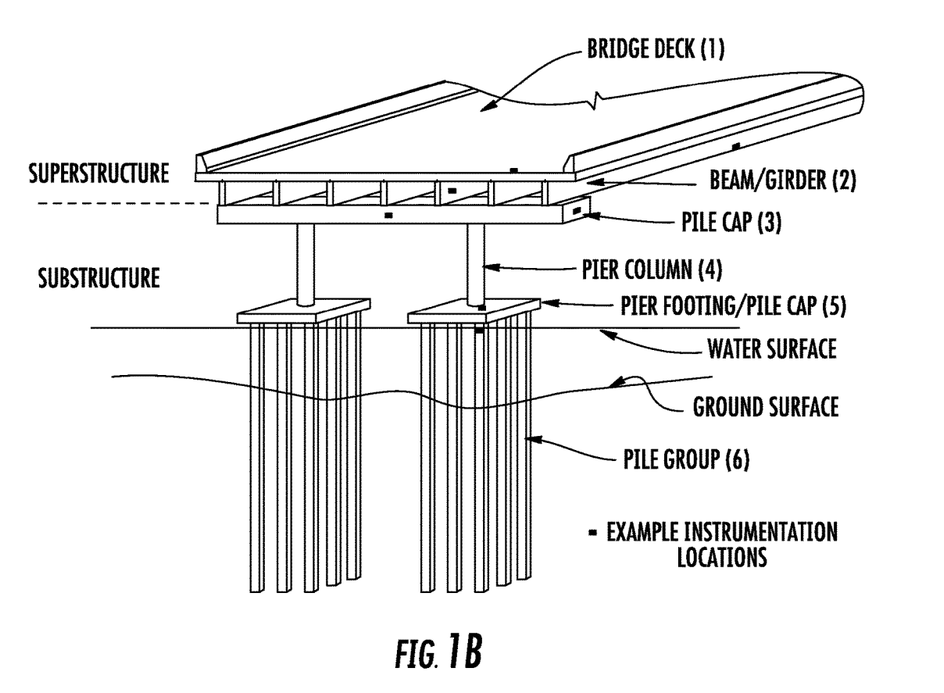
FIG. 1b illustrates a bridge pier construction.

FIG. 1b illustrates a bridge pier construction. As illustrated in FIG. 1b, the superstructure generally includes the bridge deck 1 and beams/girders 2. The substructure includes the pier cap 3, pier columns 4, pile cap/pier footing 5, and piles 6 with known or unknown embedment depth. Drilled shafts may be used instead of piles. During service, the loads are transferred from the bridge deck to the soil via the beams/girders, pier cap, pier columns, pile (shaft) cap/footing and then the piles (shafts).

Load rating procedures currently in use only target superstructure and are based on theoretical calculations and/or actual load testing.

According to the present invention, a new load rating system is provided to account for a load carrying capacity for both superstructure and substructure.

Figure 2:
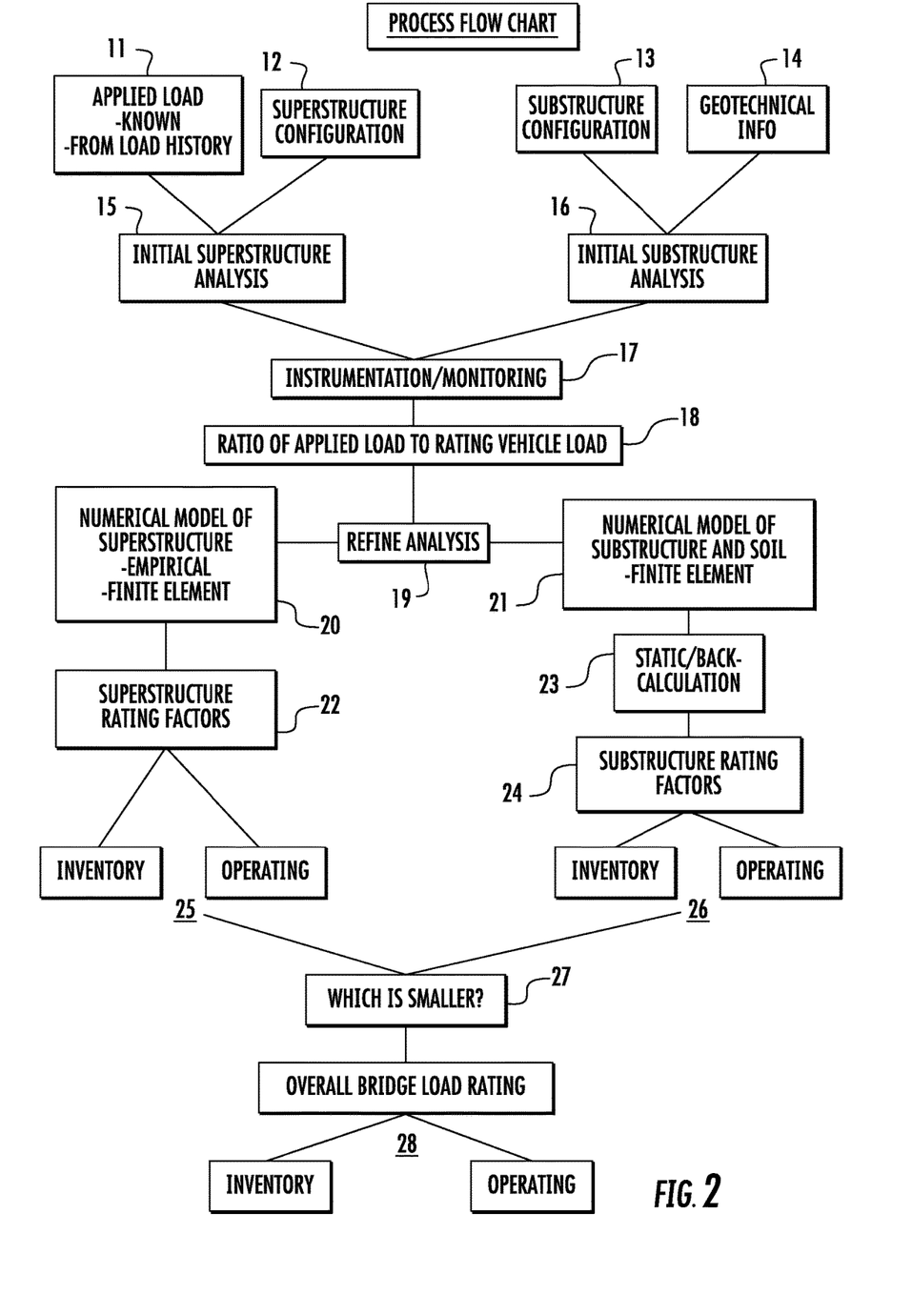
FIG. 2 is a flowchart of the proposed load rating process.

FIG. 2 is a flow chart of the proposed load rating process. As shown, applied load whether known or inferred from load history 11 along with details of the superstructure configuration 12 is used to perform an initial superstructure analysis 15. Similarly, the substructure configuration 13 along with geotechnical information 14 is used to perform an initial substructure analysis 16. This is followed by instrumentation and monitoring 17, and determination of the ratio of applied loading to that produced by the rating vehicle 18. The previous analysis is then refined 19 based on the results of the instrumentation/monitoring program. Numerical methods or empirical calculations 20 are used to derive the superstructure load rating or rating factors 22. A numerical model of the substructure and soil based on finite element is developed 21. Static/Back-Calculation (S/B-C) methodology 23 accounting for the interaction of the substructure with the soil is used to derive substructure rating factors 24 as defined by the accepted deformation criteria. Inventory and operating load ratings are calculated for both the superstructure 25 and the substructure 26. The superstructure load ratings and substructure load ratings are then compared 27 and overall bridge load ratings are established 28.

An instrumentation system including load cells, transducers, accelerometers, and/or other displacement, deformation, and force measuring instruments is used in conjunction with signal conditioning, data recording/reduction and analysis to refine the predictions and estimate actual substructure and superstructure load ratings. A camera tied to the instrumentation system may be used to verify the class of vehicle causing the loading. Transmission of data from instrumentation to data recording/reduction equipment can be wired or wireless.

Deformation and force measurements are strategically taken at critical locations on the bridge deck, beams/girders, and the pier or bent substructure components where the live loads significantly affect these components. Specific locations for instrumentation are dependent on structure configuration and results of initial analysis.

Instrumentation is efficiently mounted to minimize secondary sources inducing deformation/forces.

Monitoring can be continuous, intermittent, or short term.

Loading that would result in a prescribed response level for both superstructure and a substructure key element is derived from analysis of the instrumentation data and corresponding observed or measured loading.

Available live load carrying capacity of the structure is then determined for the superstructure and the substructure as the load in excess of dead load that results in the prescribed level of response, such as an overstressed superstructure element or deformation of the substructure.

Deformation criteria have been developed for the substructure components to define inventory and operating load rating of the substructure, similar to the inventory and operating load ratings conventionally provided for the superstructure. The criteria associate inventory rating with preventing functional failure of the foundation and operating load rating with preventing catastrophic failure of the foundation.

The inventory and operating substructure rating is used in conjunction with the inventory and operating superstructure rating to determine an overall load rating for the bridge both for inventory and operating load levels.

A Rating Factor (RF) is calculated as the ratio of the available live load carrying capacity of the structure to the response generated by the vehicle used in determining the load rating. The load rating is considered to be the Rating Factor multiplied by weight of the rating vehicle.

Load rating documentation includes bridge background data, instrumentation system description, deformation criteria, load rating predictions, comparison of predicted versus measured performance and recommendations for load rating/posting limits.

A combined analytical (numerical methods or empirical calculations) and measured load rating for the superstructure and substructure in a single process that can be done via short-term, intermittent, or long-term monitoring schemes is a major advancement in load rating for bridges.

The system can be used with both new and existing bridges and can be used to establish the potential for re-use of existing piled (shaft) foundations.

The load history is measured.

The dead load effects are those in absence of live loading on the bridge, and will correspond to the minimum effects measured by the instrumentation system during the monitoring period.

The live load effects are the maximum effects in excess of the dead load effects as measured by the instrumentation system during the monitoring period.

Applied live load is related to rating vehicle through established statistical relationships that take into account the duration of the monitoring period.

Figure 3:
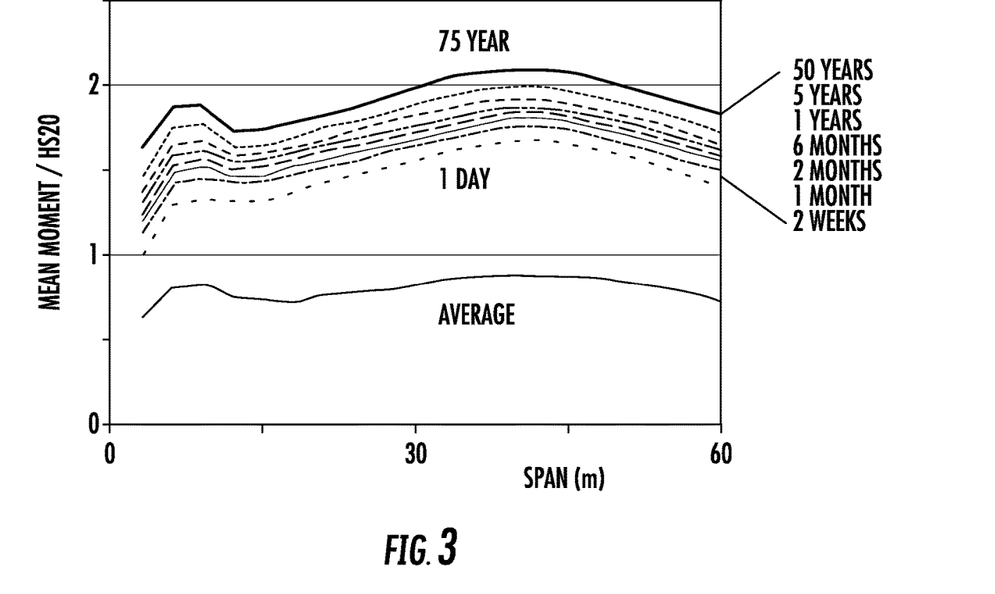
FIG. 3 shows the relationship between mean maximum superstructure moment produced by truck traffic for simple span bridges compared to that produced by the HS20 truck for different span lengths and duration of study period.
Figure 4:
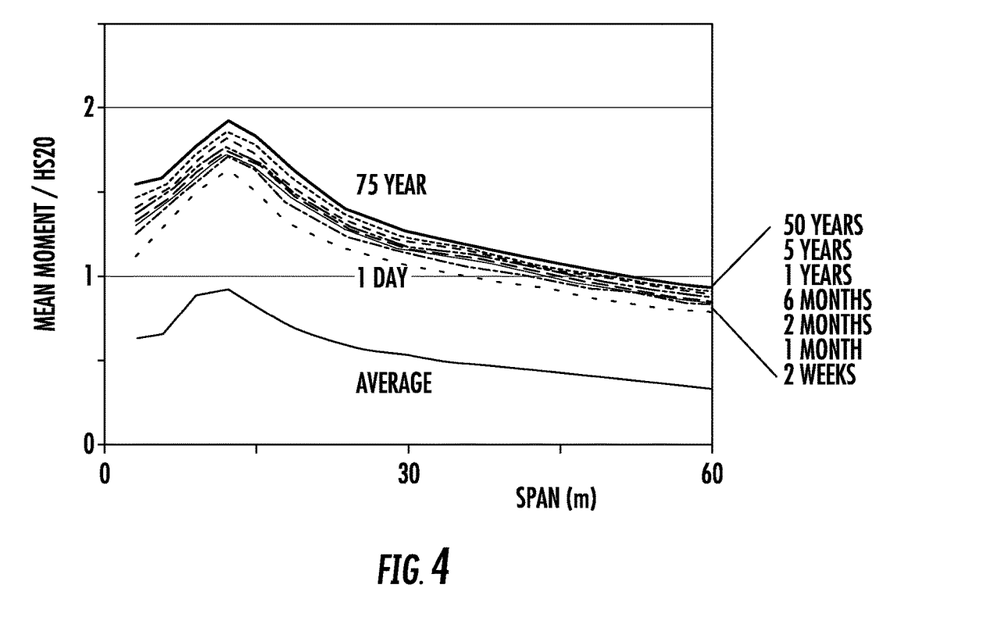
FIG. 4 shows the relationship between mean maximum negative superstructure moment produced by truck traffic for continuous span bridges compared to that produced by the HS20 truck for different span lengths and duration of study period.
Figure 5:
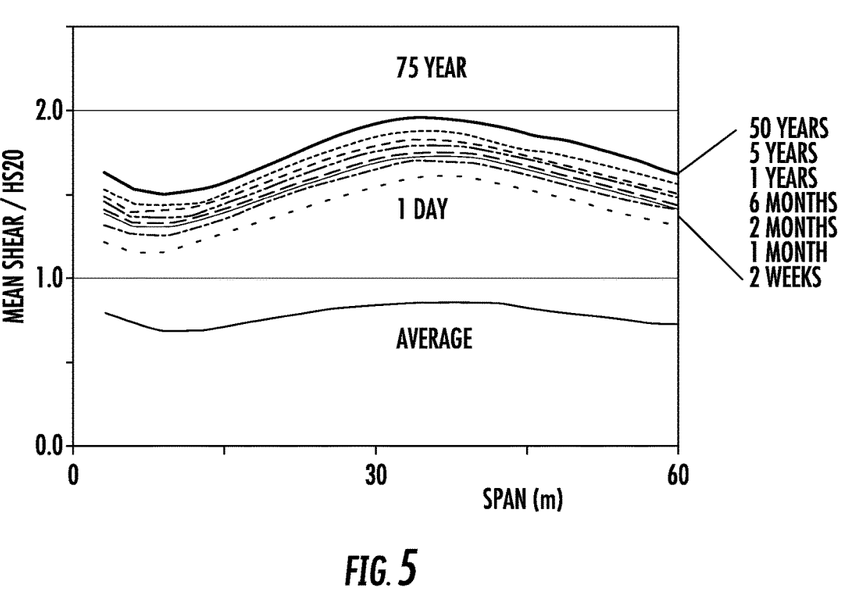
FIG. 5 shows the relationship between mean maximum superstructure shear produced by truck traffic for simple span bridges compared to that produced by the HS20 truck for different span lengths and duration of study period.

The Maximum Moment/HS20 Moment Factor is determined from FIG. 3 or 4 as a function of span, continuity, and duration, or the Maximum Shear/HS20 Shear Factor is determined from FIG. 5 as a function of span and duration.

If the load applied to the bridge is known it can be used in the embodiment of the invention.

Load effect due to the rating vehicle (e.g. HS20) is deduced from the measured effects and the established ratio of the effect of the rating vehicle to the measured effects for the monitoring period, considering the span length and continuity condition.

The superstructure rating factor is the multiple of the rating vehicle that would cause maximum prescribed effects or response in the superstructure, including rating factors specified by AASHTO.

As a first non-limiting example of the application of the invention for the superstructure load rating, a setup similar to FIG. 1 is considered where strain is measured at the point of maximum positive moment of the superstructure, typically mid-span at the bottom of the beam for a simple-span beam bridge.

The strain effect, $\varepsilon$, is measured using a strain sensor over a period of, for example, 1 day for a 30-m simple span. However, other time periods could be used.

A maximum strain at the location will occur simultaneously with maximum moment.

Stress, $\sigma$, $=\varepsilon$ times Modulus of Elasticity, E, for the beam material and is also equal to Moment, M, divided by Section Modulus, S.

S is calculated as the Moment of Inertia, I, of the composite section including the beam and tributary area of bridge deck slab divided by the distance, y, from the bottom beam fiber where the sensor is mounted to the neutral axis of the section.

$\varepsilon_o$ is considered as the strain in absence of traffic, which will be the lowest strain measured by the sensor, and will be the reference strain in the presence of dead load only. The highest strain measured by the sensor within the monitoring period=$\varepsilon_{max}$.

Given this, the strain due to the maximum truck traffic will be $\varepsilon_{max}-\varepsilon_o$.

The moment due to Truck Traffic is calculated as $M_{TR}=(\varepsilon_{max}-\varepsilon_o)\times$Modulus of Elasticity, E, x Section Modulus, S.

From FIG. 3, available in literature from Novak, Andrezej S., "Live Load Model of Highway Bridges", Journal of Structural Safety, 1993, pp 53-56, the Moment Factor=1.5. Accordingly, Moment$_{HS-20}$=Moment due to truck traffic/Moment Factor=$M_{TR}/1.5$.

Let $\sigma_{ULT}$ be the failure stress, which is typically a known quantity as defined by AASHTO and $\sigma_{HS-20}$=Moment$_{HS-20}/S$ This results in a Rating Factor for HS-20, RF$_{HS-20}$=($\sigma_{ULT}/\sigma_{HS-20}$)/LL Factor, where LL Factor=1.3 for Operating Rating and 2.17 for Inventory Rating.

Similar equations in AASHTO may be applied to the Load and Resistance Factor Rating (LRFR), where the HS-20 truck is equivalent to the LRFR HL-93 truck.

As a second non-limiting example of the application of the invention for the superstructure load rating, a setup similar to FIG. 1 is again considered where strain is measured at the point of maximum negative moment, i.e. at the top of the bridge deck over the support of the superstructure for a continuous span bridge.

Here, strain effect, $\varepsilon$, is measured using a strain sensor over a period of, for example, 1 day for a 60-m span. However, other time periods could be used.

A maximum strain at the location will occur simultaneously with maximum negative moment.

$$\sigma = \varepsilon \times E \text{(for the deck material)} = M/S_T$$

$S_T$=I divided by the distance, $y_T$, from the top slab fiber where the sensor is mounted to the neutral axis of the section.

$\varepsilon_o$ is the strain in absence of traffic, which will be the lowest strain measured by the sensor, and will be the strain due to dead load only. Let the highest strain measured by the sensor within the monitoring period=$\varepsilon_{max}$.

Then the strain due to the maximum truck traffic will be $(\varepsilon_{max}-\varepsilon_o)$ and the corresponding moment will be $$M_{TR} = (\varepsilon_{max} - \varepsilon_o) \times E \times S_T$$

From FIG. 4, available in literature from Novak, Andrezej S., "Live Load Model of Highway Bridges", Journal of Structural Safety, 1993, pp 53-56, Moment Factor=0.8, which is the ratio of the moment due to truck traffic to that caused by the HS20 truck.

$$\text{Moment}_{HS-20} = M_{TR}/0.8$$

For $\sigma_{ULT}$ as the failure stress and $$\sigma_{HS-20} = \text{Moment}_{HS-20}/S$$

This results in a Moment Rating Factor for HS-20, $RF_{HS-20} = (\sigma_{ULT}/\sigma_{HS-20})/\text{LL Factor}$, where LL Factor=1.3 for Operating Rating and 2.17 for Inventory Rating.

Similarly as a third non-limiting application example Shear is measured using load cells at the support of a simple span beam. $V_o$ will be considered the shear in absence of traffic, which will be the lowest shear measured by the load cells, and let the highest shear measured by the load cells within the monitoring period=$V_{max}$.

Then the shear due to the maximum truck traffic, $V_{TR}$, will be $V_{max}-V_o$ and the shear due to the HS-20 truck=$V_{TR}$/Shear Factor The Shear Factor is obtained from FIG. 5, available in literature from Novak, Andrezej S., "Live Load Model of Highway Bridges", Journal of Structural Safety, 1993, pp 53-56

$$V_{HS-20} = V_{TR}/\text{Shear Factor}$$

$V_{ULT}$ is considered the failure shear, which can be calculated using standard methods for known beam properties and reinforcing.

This results in a Shear Rating Factor for HS-20, $RF_{HS-20} = (V_{ULT}/V_{HS-20})/\text{LL Factor}$, where LL Factor=1.3 for Operating Rating and 2.17 for Inventory Rating The superstructure Rating Factor is the lower of the Moment Rating Factor and the Shear Rating Factor. The superstructure load rating for a rating vehicle is the Superstructure Rating Factor multiplied by the weight of the rating vehicle. For HS-20 this would be $$(RT_{HS-20})_{Sup} = (RF_{HS-20})_{Sup} \times W_{HS-20}$$

What follows is a non-limiting example of an application of the invention for the substructure load rating, where the deformation and live load ($\Delta$ and LL, respectively) are measured near the top of the substructure foundation element as shown in FIGS. 1a and 1b.

The deformation effect, $\Delta$, and the live load effect (LL) are measured using displacement gauges and a combination of stress and strain sensors from which load can be derived, respectively. $\Delta_o$ is considered the deformation during an absence of traffic, which will be the smallest deformation measured by the displacement gage, and will be the reference deformation in the presence of dead load only. $\Delta_{max}$ is the maximum deformation measured by the displacement gauge within the monitoring period. Accordingly, the deformation due to the maximum traffic ($\Delta_{TR}$) will be $$\Delta_{TR} = \Delta_{max} - \Delta_o$$

$W_{TR}$ is the maximum weight of the truck traffic.

$LL_{CT}$ is the maximum live load component/reaction for the comparable truck (CT).

$LL_{TR}$ is the maximum live load component/reaction for the maximum truck traffic.

$LL_{XXX}$ is the maximum live load component/reaction for any other truck (say $LL_{HS20}$ for truck HS20).

The substructure load rating, $(RT)_{sub}$, is then computed from the monitoring data using one of the following exemplary approaches.

Method I

Figure 6:
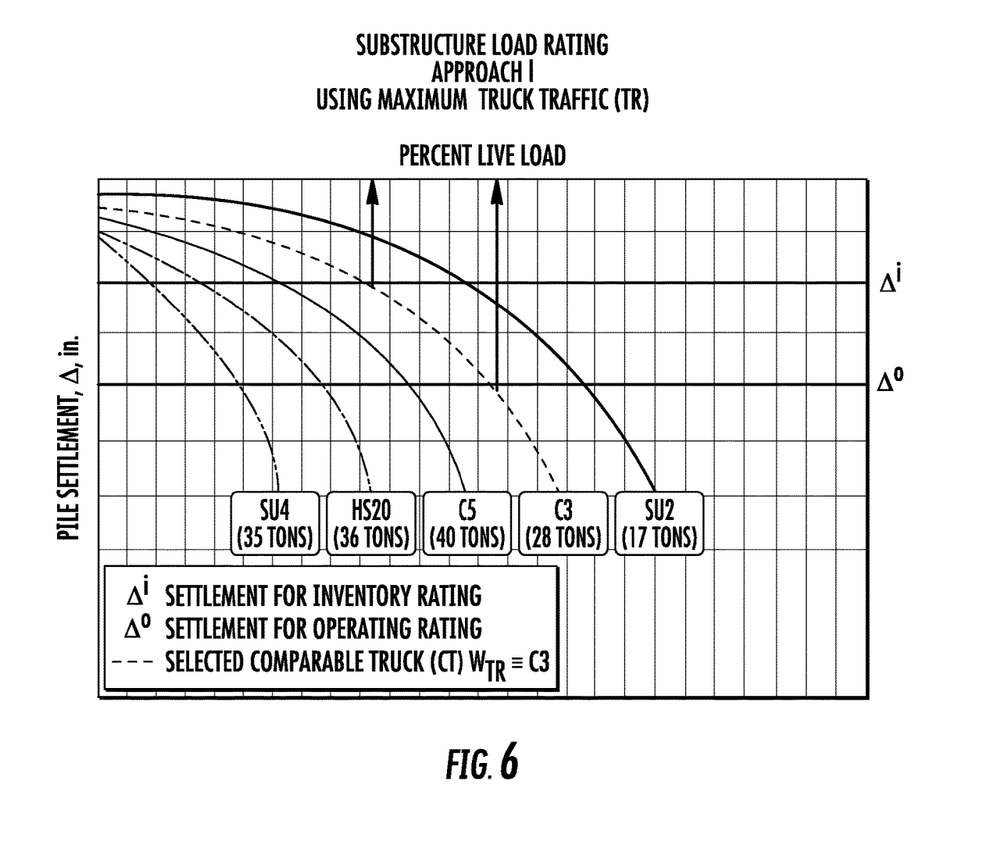
FIG. 6 shows schematic curves of the substructure load rating (pile settlement versus percent live load) for various design vehicle types illustrating the use of maximum truck traffic in the substructure load rating.

Method I uses Maximum Truck Traffic (TR) according to the following steps:

Developing the substructure load rating curves (similar to FIG. 6) using the S/B-C methodology for all rating trucks using the appropriate design methodology, for example, ASD, LFD or LRFD.

Determining the maximum truck traffic load ($W_{TR}$) from the monitoring data.

Comparing $W_{TR}$ with the weight of typical (design or rating) truck types, for example, SU2, SU3, SU4, C3, C4, C5, ST5 or HS20.

Choosing the substructure load rating curve previously developed (similar to FIG. 6) for the truck that is considered a comparable truck (CT) to the truck traffic (TR).

Determining the weight of comparable truck ($W_{CT}$).

Using the accepted deformation criteria for inventory and operating substructure load rating, respectively, to determine the corresponding % $LL_{CT}$.

% $LL_{CT}$ being the ratio of applied live load per pile (LL) to the live load per pile corresponding to the weight of the comparable truck ($LL_{CT}$).

Computing the substructure load ratings (inventory and operating) based on the comparable truck from the following expression:

$$(RT_{CT})_{sub} = \% \, LL_{CT} \times (W_{CT})$$

Computing the substructure load rating for any other vehicle type, for example HS20, from the following expression:

$$(RT_{HS20})_{sub} = (RT_{CT})_{sub} \times (LL_{CT}/LL_{HS20}) \times (W_{HS20}/W_{CT})$$

or alternatively expressed as:

$$(RT_{HS20})_{sub} = \% \, LL_{CT} \times (LL_{CT}/LL_{HS20}) \times (W_{HS20})$$

Method II

Method II uses Using Load-Deformation Monitoring Data (LL vs. $\Delta$) according to the following steps:

Determining the maximum truck traffic ($W_{TR}$) from the monitoring data.

Converting the deformation ($\Delta$) and live load (LL) monitoring data to deformation ($\Delta$) and percent live load % $LL_{TR}$.

Figure 7:
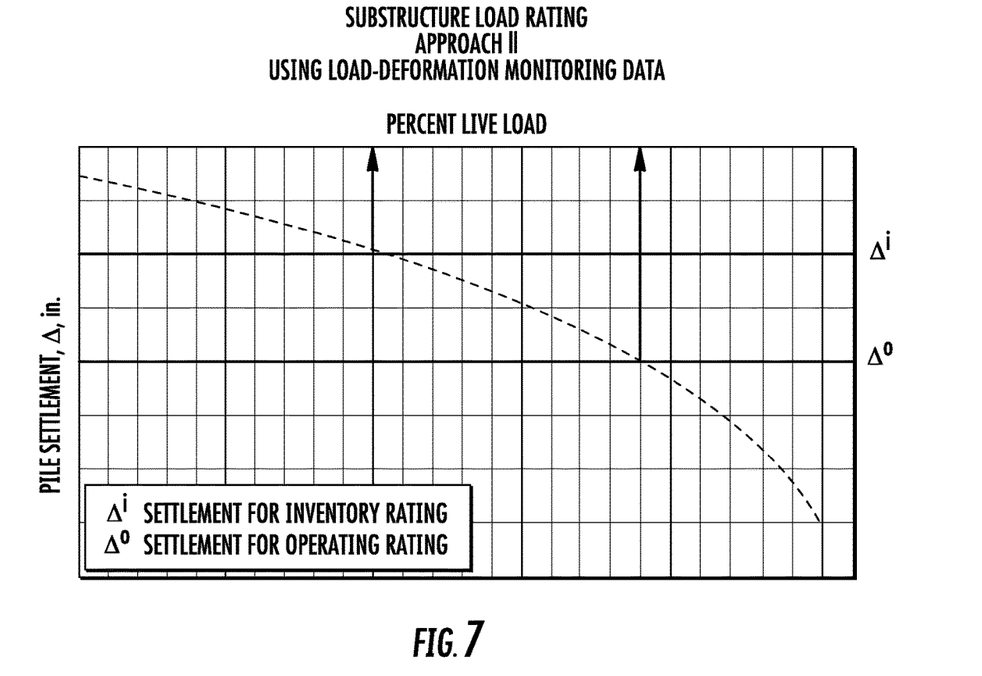
FIG. 7 shows schematic curve of the measured data (i.e., pile settlement versus percent live load) illustrating the use of the operational measurements in the substructure load rating.

Plotting $\Delta$ versus % $LL_{TR}$, as shown schematically in FIG. 7.

Using the accepted deformation criteria, determining the % LL corresponding to the inventory and operating substructure load rating.

Computing the inventory and operating substructure load rating for a nominal truck that corresponds to the maximum truck traffic ($W_{TR}$) from the following expression:

$$(RT_{TR})_{sub} = \% \, LL_{TR} \times (W_{TR})$$

% $LL_{TR}$ being the ratio of applied live load per pile (LL) to the live load per pile corresponding to the weight of the maximum truck traffic ($LL_{TR}$) within the monitoring period.

Computing the substructure load rating for any other vehicle type, for example HS20, from the following expression:

$$(RT_{HS20})_{sub} = (RT_{TR})_{sub} \times (LL_{TR}/LL_{HS20}) \times (W_{HS20}/W_{TR})$$

or alternatively expressed as:

$$(RT_{HS20})_{sub} = \% \, LL_{TR} \times (LL_{TR}/LL_{HS20}) \times (W_{HS20})$$

The superstructure load rating is combined with the substructure load rating to determine an overall load rating for the bridge.

The substructure load rating can be determined for different mudline elevations for bridges over waterways as loss of foundation soil support due to scour reduces the load carrying capacity of the substructure.

A detailed description along with case studies showing exemplary, non-limiting applications of the superstructure—substructure load rating process according to the invention is described in Sayed, Sayed M. et al., The Journal of Bridge Engineering, "*Load Rating of Pile-Supported Bridges Susceptible to Scour*", The Journal of Bridge Engineering, pages 439-449, May 2013, which is incorporated herein by reference as if fully set forth.

The superstructure—substructure load rating process according to the invention is unique because it achieves two goals, namely, it measures load carrying capacity of the superstructure and it measures the load carrying capacity of the substructure.

The invention provides a superior alternative to traditional field load testing which requires road closure, significant loading capability, and significant expense. The process also accounts for the capacity of the substructure including its interaction with the soil.

SUMMARY OF THE EMBODIMENTS

A method for load rating of pile-supported bridges with known or unknown embedment depth using a hybrid analytical system, comprising determining a pile embedment where unknown, determining a substructure load rating, determining a superstructure load rating, and calculating a bridge load rating using the substructure and superstructure load ratings.

The prior method, wherein for determining the pile embedment, the method further comprises using a Static/Back-Calculation.

One of the prior methods, wherein for determining pile embedment, applying specific safety factors or load factors.

One of the prior methods, wherein for determining pile embedment, applying specific resistance factors.

One of the prior methods, wherein for determining pile embedment, applying specific geotechnical capacity criteria.

One of the prior methods, wherein for determining pile embedment, applying specific deformation criteria.

One of the prior methods, further comprising providing a plurality of monitoring systems for measuring displacement.

One of the prior methods, further comprising providing a plurality of monitoring systems for measuring load.

One of the prior methods, further comprising providing a plurality of monitoring systems for measuring strain.

One of the prior methods, further comprising providing a plurality of monitoring systems for measuring scour.

One of the prior methods, wherein for determining substructure load rating, applying deformation criteria for inventory load rating.

One of the prior methods, wherein for determining substructure load rating, applying deformation criteria for operating load rating.

One of the prior methods, wherein for determining substructure load rating, applying a live load to a soil-structure system.

One of the prior methods, wherein for determining substructure load rating, computing displacement under the load.

One of the prior methods, wherein for determining substructure load rating, applying the substructure bridge load rating.

One of the prior methods, wherein for determining superstructure load rating, applying a specific live load.

One of the prior methods, wherein for determining superstructure load rating, applying a factor related to monitoring duration and bridge span length and continuity to relate a measured response to a response caused by a rating vehicle.

One of the prior methods, wherein for determining superstructure load rating, applying specific straining actions at specific locations in specific superstructure elements.

One of the prior methods, wherein for determining superstructure load rating, applying rating factors for specific superstructure elements.

One of the prior methods, wherein for determining superstructure load rating, applying the superstructure bridge load rating.

One of the prior methods, further comprising providing a monitoring system for the bridge metrics.

A system for carrying out one or more of the above methods, comprising measurement units, and signal conditioning and data recording/reduction devices configured for receiving data from the measurement units and calculating the bridge load rating.

The prior system, further comprising displacement sensors positioned at measurement locations on the superstructure and substructure elements.

One of the prior systems, further comprising load sensors positioned at measurement locations on the superstructure and substructure elements.

One of the prior systems, further comprising strain sensors/gauges, positioned at measurement locations on the superstructure and substructures elements.

One of the prior systems, further comprising scour detection devices positioned at measurement locations in a waterway around the substructure.

What is claimed is:

1. A method for live load rating of pile-supported bridges with known or unknown embedment depth using a hybrid analytical system, comprised of:
   determining a pile embedment of a pile supported bridge;
   using at least one of displacement gauges, stress sensors or strain sensors on at least one of piles or other substructure elements to determine a substructure load rating as vehicular traffic loads the bridge;
   using at least one of strain sensors or load cells at measurement locations on bridge superstructure elements to determine a superstructure load rating as vehicular traffic loads the bridge, wherein determining superstructure load rating, comprises applying a factor related to monitoring duration and bridge span length and continuity to relate a measured response to a response caused by a rating vehicle;

calculating an overall bridge load rating by combining the substructure and the superstructure load ratings; and outputting the overall bridge load rating.

2. The method of claim 1, wherein determining the pile embedment, the method further comprises using a Static/Back-Calculation for determining an estimated pile embedment.

3. The method of claim 1, wherein for determining pile embedment, the method further comprises applying specific safety factors or load factors.

4. The method of claim 1, wherein for determining pile embedment, the method further comprises applying specific resistance factors.

5. The method of claim 1, wherein for determining pile embedment, the method further comprises applying specific geotechnical capacity criteria.

6. The method of claim 1, wherein for determining pile embedment, the method further comprises applying specific deformation criteria.

7. The method of claim 1, further comprising providing a plurality of monitoring systems for measuring scour.

8. The method of claim 1, wherein for determining substructure load rating, the method further comprises applying deformation criteria for inventory load rating.

9. The method of claim 1, wherein for determining substructure load rating, the method further comprises applying deformation criteria for operating load rating.

10. The method of claim 1, wherein for determining substructure load rating, the method further comprises applying a live load to a soil-structure system.

11. The method of claim 1, wherein for determining substructure load rating, the method further comprises computation of displacement under the load.

12. The method of claim 1, wherein for determining superstructure load rating, the method further comprises applying rating factors for specific superstructure elements.

13. A system for carrying out the method of claim 1, comprising signal conditioning and data recording/reduction devices configured for receiving data from the at least one of displacement gauges, stress sensors or strain sensors and the at least one of strain sensors or load cells and calculating the bridge load rating.

14. The system of claim 1, further comprising scour detection devices positioned at measurement locations in a waterway around the substructure.

\* \* \* \* \*